(12) United States Patent
Shelton, IV et al.

(10) Patent No.: US 8,241,209 B2
(45) Date of Patent: Aug. 14, 2012

(54) ACTIVE SEAL COMPONENTS

(75) Inventors: Frederick E. Shelton, IV, Hillsboro, OH (US); Charles J. Scheib, Loveland, OH (US); Jerome R. Morgan, Cincinnati, OH (US); Carl J. Shurtleff, Mason, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 433 days.

(21) Appl. No.: 12/479,092

(22) Filed: Jun. 5, 2009

(65) Prior Publication Data
US 2010/0312065 A1 Dec. 9, 2010

(51) Int. Cl.
*A61B 1/32* (2006.01)
(52) U.S. Cl. ...................................................... 600/207
(58) Field of Classification Search .................. 600/201, 600/206, 207, 208
See application file for complete search history.

(56) References Cited

U.S. PATENT DOCUMENTS

| | | |
|---|---|---|
| 2,129,391 A | 9/1938 | Wappler |
| 3,402,710 A | 9/1968 | Paleschuck |
| 3,654,965 A | 4/1972 | Gramain |
| 4,112,932 A | 9/1978 | Chiulli |
| 4,306,545 A | 12/1981 | Ivan et al. |
| 4,379,458 A | 4/1983 | Bauer et al. |
| 4,402,683 A | 9/1983 | Kopman |
| 4,417,888 A | 11/1983 | Cosentino et al. |
| 5,010,925 A | 4/1991 | Atkinson et al. |
| 5,091,435 A | 2/1992 | Suzuki et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |
| 5,269,772 A | 12/1993 | Wilk |
| 5,308,336 A | 5/1994 | Hart et al. |
| 5,312,417 A | 5/1994 | Wilk |

(Continued)

FOREIGN PATENT DOCUMENTS
DE    19814576 A1    10/1999
(Continued)

OTHER PUBLICATIONS

U.S. Appl. No. 12/420,107 ("Retractor with Flexible Sleeve" of Shelton et al.).

(Continued)

*Primary Examiner* — Sunil K Singh
(74) *Attorney, Agent, or Firm* — Nutter McClennen & Fish LLP

(57) ABSTRACT

Methods and devices are provided to allow for easy manipulation of a configuration and/or an orientation of seal elements of a surgical access device by an end user. In one exemplary embodiment a surgical access device is provided that includes a retractor configured to be positioned within a surgical incision to provide access to a body cavity, seal elements disposed within a lumen of the retractor, and adjustment mechanisms in communication with the seal elements and which are configured to manipulate an orientation of one or more of the seal elements. Types of adjustment mechanisms capable of manipulating the seal elements as desired include inflatable bladders and electroactive polymers. Exemplary methods for providing easy manipulation of the configuration and/or orientation of seal elements of a surgical access device on location are also provided.

16 Claims, 6 Drawing Sheets

U.S. PATENT DOCUMENTS

| | | |
|---|---|---|
| 5,320,611 A | 6/1994 | Bonutti et al. |
| 5,342,315 A | 8/1994 | Rowe et al. |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,522,791 A * | 6/1996 | Leyva ............... 600/207 |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,797,888 A | 8/1998 | Yoon |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,990,382 A | 11/1999 | Fox |
| 5,997,515 A | 12/1999 | de la Torre et al. |
| 6,024,736 A | 2/2000 | de la Torre et al. |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 2002/0156432 A1 | 10/2002 | Racenet et al. |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0082969 A1 | 4/2004 | Kerr |
| 2004/0106942 A1 | 6/2004 | Taylor et al. |
| 2004/0117032 A1 | 6/2004 | Roth |
| 2004/0138528 A1 | 7/2004 | Richter et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 | 2/2006 | Ewers et al. |
| 2006/0071432 A1 | 4/2006 | Staudner |
| 2006/0129165 A1 | 6/2006 | Edoga et al. |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1 | 11/2006 | Bonadio et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |

| | | | | | | |
|---|---|---|---|---|---|---|
| 2007/0085232 A1 | 4/2007 | Brustad et al. | | EP | 1731105 A1 | 12/2006 |
| 2007/0088202 A1 | 4/2007 | Albrecht et al. | | EP | 1774918 A1 | 4/2007 |
| 2007/0088204 A1 | 4/2007 | Albrecht et al. | | EP | 2119404 A1 | 11/2009 |
| 2007/0088258 A1 | 4/2007 | Wenchell et al. | | FR | 2710270 A1 | 3/1995 |
| 2007/0088277 A1 | 4/2007 | McGinley et al. | | JP | 2006320750 | 11/2006 |
| 2007/0118021 A1 | 5/2007 | Pokorney | | WO | 9407552 A1 | 4/1994 |
| 2007/0118175 A1 | 5/2007 | Butler et al. | | WO | 9602297 A1 | 2/1996 |
| 2007/0151566 A1 | 7/2007 | Kahle et al. | | WO | 9608897 A1 | 3/1996 |
| 2007/0185453 A1 | 8/2007 | Michael et al. | | WO | 9636283 A1 | 11/1996 |
| 2007/0208312 A1 | 9/2007 | Norton et al. | | WO | 9743958 A1 | 11/1997 |
| 2007/0255219 A1 | 11/2007 | Vaugh et al. | | WO | 0032263 A1 | 6/2000 |
| 2008/0009797 A1 | 1/2008 | Stellon et al. | | WO | 0041759 A1 | 7/2000 |
| 2008/0025519 A1 | 1/2008 | Yu et al. | | WO | 0108563 A2 | 2/2001 |
| 2008/0027476 A1 | 1/2008 | Piskun | | WO | 0217800 A2 | 3/2002 |
| 2008/0051739 A1 | 2/2008 | McFarlane | | WO | 2004030515 A2 | 4/2004 |
| 2008/0058728 A1 | 3/2008 | Soltz et al. | | WO | 200500454 A1 | 1/2005 |
| 2008/0065021 A1 | 3/2008 | Jenkins et al. | | WO | 2005002454 A1 | 1/2005 |
| 2008/0086080 A1 | 4/2008 | Mastri et al. | | WO | 2005087112 A1 | 9/2005 |
| 2008/0119821 A1 | 5/2008 | Agnihotri et al. | | WO | 2005094432 A2 | 10/2005 |
| 2008/0132765 A1 | 6/2008 | Beckman et al. | | WO | 2005097019 A2 | 10/2005 |
| 2008/0255519 A1 | 10/2008 | Piskun et al. | | WO | 2005097234 A2 | 10/2005 |
| 2008/0281161 A1 | 11/2008 | Albrecht et al. | | WO | 2006057982 A2 | 6/2006 |
| 2009/0005799 A1 | 1/2009 | Franer et al. | | WO | 2007008741 A1 | 1/2007 |
| 2009/0082731 A1 | 3/2009 | Moreno | | WO | 2007119232 A2 | 10/2007 |
| 2009/0118587 A1 | 5/2009 | Voegele et al. | | WO | 2008024502 A2 | 2/2008 |
| 2009/0187079 A1 | 7/2009 | Albrecht et al. | | WO | 2008028149 A2 | 3/2008 |
| 2009/0270685 A1 | 10/2009 | Moreno et al. | | WO | 2008121294 A1 | 10/2008 |
| 2009/0270686 A1 | 10/2009 | Duke et al. | | WO | 2009035663 A2 | 3/2009 |
| 2009/0270818 A1 | 10/2009 | Duke | | | | |
| 2010/0010310 A1 | 1/2010 | Weisenburgh, II et al. | | | | |
| 2010/0081863 A1 | 4/2010 | Hess et al. | | | | |
| 2010/0081864 A1 | 4/2010 | Hess et al. | | | | |
| 2010/0081871 A1 | 4/2010 | Widenhouse et al. | | | | |
| 2010/0081880 A1 | 4/2010 | Widenhouse et al. | | | | |
| 2010/0081881 A1 | 4/2010 | Murray et al. | | | | |
| 2010/0081882 A1 | 4/2010 | Hess et al. | | | | |
| 2010/0081883 A1 | 4/2010 | Murray et al. | | | | |
| 2010/0081995 A1 | 4/2010 | Widenhouse et al. | | | | |
| 2010/0228090 A1 | 9/2010 | Weisenburgh, II et al. | | | | |
| 2010/0228091 A1 | 9/2010 | Widenhouse et al. | | | | |
| 2010/0228092 A1 | 9/2010 | Ortiz et al. | | | | |
| 2010/0228094 A1 | 9/2010 | Ortiz et al. | | | | |
| 2010/0228096 A1 | 9/2010 | Weisenburgh, II et al. | | | | |
| 2010/0228198 A1 | 9/2010 | Widenhouse et al. | | | | |
| 2010/0249525 A1 | 9/2010 | Shelton, IV et al. | | | | |
| 2010/0261970 A1 | 10/2010 | Shelton, IV et al. | | | | |
| 2010/0261972 A1 | 10/2010 | Widenhouse et al. | | | | |
| 2010/0261974 A1 | 10/2010 | Shelton, IV et al. | | | | |
| 2010/0262080 A1 | 10/2010 | Shelton, IV et al. | | | | |
| 2010/0268162 A1 | 10/2010 | Shelton, IV et al. | | | | |
| 2010/0274093 A1 | 10/2010 | Shelton, IV | | | | |
| 2010/0280327 A1 | 11/2010 | Nobis et al. | | | | |
| 2010/0312060 A1 | 12/2010 | Widenhouse et al. | | | | |
| 2010/0312061 A1 | 12/2010 | Hess et al. | | | | |
| 2010/0312062 A1 | 12/2010 | Cropper et al. | | | | |
| 2010/0312063 A1 | 12/2010 | Hess et al. | | | | |
| 2010/0312064 A1 | 12/2010 | Weisenburgh, II et al. | | | | |
| 2010/0312065 A1 | 12/2010 | Shelton, IV et al. | | | | |
| 2010/0312066 A1 | 12/2010 | Cropper et al. | | | | |
| 2010/0312189 A1 | 12/2010 | Shelton, IV et al. | | | | |

FOREIGN PATENT DOCUMENTS

| | | | |
|---|---|---|---|
| DE | 20022005 U1 | 4/2001 | |
| EP | 568383 A1 | 11/1993 | |
| EP | 577400 A1 | 1/1994 | |
| EP | 0637431 A1 | 2/1995 | |
| EP | 646358 A1 | 4/1995 | |
| EP | 709918 | 5/1996 | |
| EP | 0776231 B1 | 6/1997 | |
| EP | 950376 | 10/1999 | |
| EP | 1219251 A1 | 7/2002 | |
| EP | 1219252 A1 | 7/2002 | |
| EP | 1219253 A1 | 7/2002 | |
| EP | 1350476 | 10/2003 | |
| EP | 1702575 A2 | 9/2006 | |

OTHER PUBLICATIONS

U.S. Appl. No. 12/420,202 ("Surgical Access Device Having Removable and Replaceable Components" of Shelton et al.).

International Search Report and Written Opinion for International App. No. PCT/US2010/036811 dated Sep. 14, 2010 (6 pages).

International Search Report, from PCT/US10/36829, mailed Sep. 9, 2010 (5 pages).

European Search Report, EP 10250732, dated Jul. 28, 2010.

International Search Report and Written Opinion for Application No. PCT/US2010/037190, dated Sep. 22, 2010 (15 pages).

"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport > R-Port laparoscopic access device > Advanced Surgical Concepts ASC" Ideas for Surgery.com, Dec. 2007, 4 pages.

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp: 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp: 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

International Search Report and Written Opinion for Application No. PCT/US2010/036806, dated Sep. 3, 2010 (8 pages).

International Search Report and Written Opinion for Application No. PCT/US2010/036820, dated Oct. 22, 2010 (18 pages).

* cited by examiner

ACTIVE SEAL COMPONENTS

FIELD

The present invention relates to methods and devices for accessing a surgical site, and more particularly to methods and devices that allow for the configuration and/or orientation of a surgical seal element to be manipulated on location prior to and/or during a surgical procedure.

BACKGROUND

Minimally invasive surgical techniques such as endoscopies and laparoscopies are often preferred over traditional open surgeries because the recovery time, pain, and surgery-related complications are typically less with minimally invasive surgical techniques. In many laparoscopic procedures, the abdominal cavity is insufflated with carbon dioxide gas to a pressure of approximately 15 mm Hg. The abdominal wall is pierced and a cannula or trocar that is approximately 5 to 10 mm in diameter is inserted into the abdominal cavity. Surgeons can then perform a variety of diagnostic procedures, such as visual inspection or removal of a tissue sample for biopsy, or treatment procedures, such as removal of a polyp or tumor or restructuring tissue.

Because of the rise in popularity of minimally invasive surgeries, there has been significant development with respect to the procedures and the instruments used in such procedures. For example, in some procedures a single incision at the navel can be sufficient to provide access to a surgical site. This is because the umbilicus can be a preferred way to access an abdominal cavity in a laparoscopic procedure. The umbilical incision can be easily enlarged without significantly compromising cosmesis and without significantly increasing the chances of wound complications, thus allowing multiple instruments to be introduced through a single incision.

While single site laparoscopy procedures are often desirable, the use of multiple instruments in a small area can provide a number of complications, including space and ease of use issues. By way of non-limiting example, it can be difficult to apply opposed forces to a surgical site, such as forces related to suturing. Another possible drawback to current devices used in single site laparoscopic procedures is that they are generally prefabricated to assume a particular configuration. It would be desirable to allow a surgeon to easily adjust a size, shape, and/or location of one or more seal elements of a surgical access device based on the needs of a particular procedure being performed on a particular patient.

SUMMARY

Methods and devices are generally provided that allow a surgeon to easily manipulate the configuration and/or orientation of one or more seal elements of a surgical access device during a surgical procedure. In one embodiment a surgical access device includes a retractor having a sidewall that defines a central lumen. The retractor can be configured in a manner that allows it to be positioned within a surgical incision, thereby providing access to a body cavity. The device can also include at least one seal element disposed within the lumen of the retractor. The seal element can have a configuration that is effective to seal the lumen. The seal element can include a sealable opening that can be configured to receive a surgical instrument in a sealing engagement. The surgical access device can further include at least one adjustment mechanism that is in communication with the seal element. The adjustment mechanism can be configured in a manner that allows it to manipulate an orientation of the seal element.

The adjustment mechanism can have a variety of different configurations, but it is typically an element that is capable of selectively changing its shape and dimensions. In one embodiment the adjustment mechanism can include an expandable bladder positioned adjacent to at least one seal element. In another embodiment the adjustment mechanism can include an electroactive polymer positioned adjacent to at least one seal element. The expandable bladder and the electroactive polymer can each be configured such that expansion and/or contraction thereof can control the orientation of the adjacent sealing element. In still another embodiment of a surgical access device, the seal element itself can be configured to expand and contract based on a direct input. In such an embodiment an adjustment mechanism of the surgical access device can include a valve configured to regulate an amount of fluid in the seal element.

The opening of the seal element can have a variety of different shapes, configurations, and sizes. Two examples of shapes for the seal element include an elongate opening and a substantially circular opening. In one embodiment the surgical access device further includes a seal control mechanism in communication with at least one of the at least one seal element and the at least one adjustment mechanism. The seal element(s) can be removably and replaceably mounted in the retractor.

One exemplary embodiment of a method for accessing a surgical site includes providing a retractor having one or more seal elements disposed therein. The one or more seal elements can each include an opening formed therein. The retractor can also include one or more expandable elements adjacent to the one or more seal elements. The method can further include positioning the retractor through an opening in tissue. At least one surgical instrument can be inserted into one of the openings in the seal elements. Further, a configuration of at least one of the one or more seal elements can be selectively adjusted by expanding and/or contracting the one or more expandable elements, thereby controlling at least one of the size and the shape of the opening in the seal element. In one embodiment a distal end of the retractor can be expanded and/or contracted to assist in positioning the retractor through an opening in tissue. In another embodiment a surgical site can be insufflated through at least one of the openings in the one or more seal elements.

Another exemplary embodiment of a method for accessing a surgical site also includes providing a retractor having one or more seal elements disposed therein. The one or more seal elements can each include an opening formed therein. The retractor can also include one or more electroactive polymers adjacent to the one or more seal elements. The method can further include positioning the retractor through an opening in tissue. At least one surgical instrument can be inserted into one of the openings in the seal elements. Further, a configuration of at least one of the one or more seal elements can be selectively adjusted by applying a voltage to the one or more electroactive polymers, thereby controlling at least one of the size and the shape of the opening in the seal element. In one embodiment a distal end of the retractor can be expanded and/or contracted to assist in positioning the retractor through an opening in tissue. In another embodiment a surgical site can be insufflated through at least one of the openings in the one or more seal elements.

BRIEF DESCRIPTION OF DRAWINGS

This invention will be more fully understood from the following detailed description taken in conjunction with the accompanying drawings, in which.

DETAILED DESCRIPTION

Figure 1:
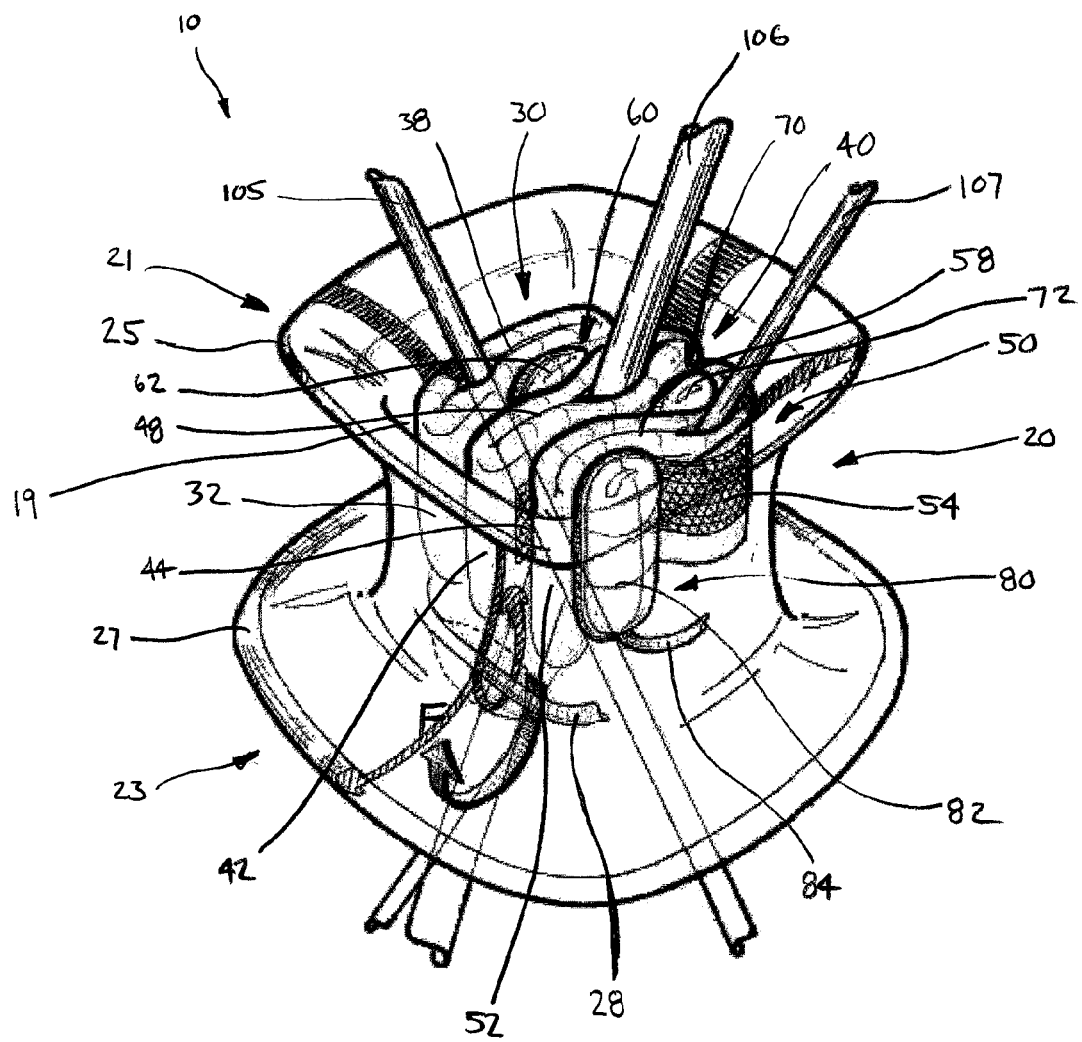
FIG. 1 is a partially transparent perspective view of one exemplary embodiment of a surgical access device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A surgical access device is generally provided for minimally-invasive surgeries such as laparoscopic surgeries. The surgical access device can be disposed in a body to allow for access to a surgical site from outside of the body. The device can generally be configured to receive one or more instruments through the device so that the instruments can be used to perform a desired procedure. The device can have a number of different components, but in an exemplary embodiment a surgical access device includes a retractor having a sidewall that defines a central lumen, one or more seal elements disposed within at least a portion of the lumen of the retractor, and at least one adjustment mechanism in communication with the seal element(s) and configured to manipulate an orientation of the seal element(s). While the term "orientation" is generally used with respect to a size and shape of a single seal element and the term "configuration" is generally used to refer to how a seal element is situated with respect to other seal elements of a surgical access device, these words can be used interchangeably.

The retractor of the surgical access device can provide access to a surgical location, such as a body cavity, from an outside location by way of a configuration that can allow it to be positioned within a surgical incision. The retractor, in conjunction with the seal element(s), can form a seal between the surgical location and the outside environment. The retractor can also form a seal between the tissue of the incision in which it is disposed and the retractor itself.

The seal element(s) can be configured in a manner that allows each seal element to effectively seal the lumen of the retractor, thereby maintaining a seal between the surgical location and the outside environment. A seal between the surgical location and the outside environment can be maintained during insertion, removal, and use of a surgical instrument. The seal element(s) can further include a sealable opening that can be configured to receive a surgical instrument. The sealable opening can be configured in a manner that allows the seal element form a seal when a surgical instrument is absent and to maintain the seal by forming a sealing engagement with a surgical instrument disposed through the sealable opening. In one exemplary embodiment the seal element(s) can be configured to allow the orientation of one or more seal elements to be adjusted prior to or during a surgical procedure. Adjustment of the orientation of the seal element(s) can include, but is not limited to, adjustment of the size and shape of the seal element(s).

The adjustment mechanism, which is in communication with the seal element(s), can assist in adjusting the orientation of one or more of the seal elements. A variety of different mechanisms can be used to manipulate the orientation of the seal element(s), examples of which will be more fully described herein. In some embodiments the adjustment mechanism can be integrally formed with the seal elements. Further, a seal control mechanism, such as a valve, can optionally be associated with the adjustment mechanism to help regulate or control the inputs made by the adjustment mechanism to the seal elements. In some embodiments the seal control mechanism can be integrally formed with the adjustment mechanism, and further, in some embodiments the adjustment mechanism and the seal control mechanism can both be integrally formed with the seal elements.

The described surgical access devices can allow for an end user, such as a surgeon, to adjust the configuration and/or orientation of the device's seal element(s) for the particular needs of a particular surgery. The orientation of a single seal element can be manipulated, or alternatively, the orientations of multiple seal elements of a surgical access device can be coordinated to achieve a desired configuration for the surgical access device. The ability to adjust the orientation of seal elements during a surgical procedure without removing the seal elements can be particularly advantageous.

FIG. 1 illustrates one exemplary embodiment of a surgical access device 10 for use in surgical procedures such as a single site laparoscopy. The device 10 includes a retractor 20 that can be positioned within a surgical incision to provide access to a surgical site, such as a body cavity, one or more seal elements, as shown three seal elements 30, 40, and 50, configured to be disposed within at least a portion of the retractor 20, and at least one adjustment mechanism, as shown three adjustment mechanisms 60, 70, and 80, in communication with at least one of the seal elements 30, 40, 50 and configured to manipulate a configuration and/or orientation of the respective seal element(s) 30, 40, 50. The combination of the retractor 20, seal elements 30, 40, 50, and adjustment mechanisms 60, 70, 80 can be effective to form a seal between the surgical site and an outside environment, thereby limiting or preventing fluid from passing therebetween.

Each of the components of the surgical access device 10 can have a variety of configurations. The retractor 20, for example, can be generally configured to be disposed within an incision formed through tissue to form a working channel extending into a body cavity. The retractor 20 can form a seal between tissue in which it is disposed and the retractor 20 itself. Further, the retractor 20 defines a central lumen 19 within which the seal element(s) 30, 40, 50 are at least partially disposed. While the retractor 20 can have a variety of shapes, depending at least in part on the size of the incision in which it will be disposed, the surgical device components with which it will be used, and the type of surgical procedure with which it will be used, in one exemplary embodiment the retractor 20 is an elongate hollow cylindrical member having a proximal portion 21 and a distal portion 23 configured to retract tissue away from an incision in which it is disposed. Although the illustrated embodiments include retractors having features for retracting tissue on both sides of a surgical opening, in alternative embodiments the retractor 20 can be configured to couple to other devices. For example, the retractor 20 can be configured to be only partially disposed in an incision and can then be configured to couple to another component that extends through the remainder of the opening. Some exemplary embodiments of retractors that can be configured to couple to other components of a surgical access device are described in greater detail in U.S. Publication No. 2010/0262080 entitled "Surgical Access Device Having Removable and Replaceable Components" of Shelton et al., and filed on Apr. 8, 2009, which is hereby incorporated by reference in its entirety.

The retractor 20 can be configured to be generally flexible, and thus can be made from a flexible material, such as a polymer. Examples of flexible materials that can be used to form the retractor 20 include polyisoprene, polyurthethane, and silicone. More than one material can be used to form the retractor 20, and the retractor 20 can include some portions that are more rigid than other portions. For example, more rigid portions of a retractor can be made from materials such as polycarbonate, polyester, polyetherimide, or stainless steel, while more flexible portions can be made from materials such as polyisoprene, polyurthethane, and silicone. Another non-limiting exemplary embodiment of a retractor that can be used with the teachings described herein is described in greater detail in U.S. Publication No. 2010/0261970 entitled "Retractor with Flexible Sleeve" of Shelton et al., and filed on Apr. 8, 2009, which is hereby incorporated by reference in its entirety.

Just as the retractor 20 can have a variety of shapes, it can also have a variety of sizes. The size of the retractor 20 can depend at least on the some of the same factors that affect the shape of the retractor, including the size of the incision in which it will be disposed, surgical devices components with which it will be used, and the type of surgical procedure with which it will be used. In the illustrated embodiment the retractor 20 is configured such that both the proximal and distal portions 21 and 23 include rings 25 and 27, respectively, to assist with retracting tissue away from a surgical opening. As shown, ring 27 of the distal portion 23 has a larger diameter than the ring 25 of the proximal portion 21, but in alternative embodiments the rings 25 and 27 can have approximately similar diameters or the ring 25 of the proximal portion 21 can be larger than the ring 27 of the distal portion 23. In addition to assisting with tissue retraction, the rings 25 and 27 can provide stability to assist with holding the surgical access device 10 in an incision in which it is disposed. The rings 25 and 27 can be formed integrally with or be disposed within flanges of the proximal and/or distal portions 21, 23. In an exemplary embodiment the diameters of the proximal and distal portions 21, 23 of the retractor 20 can be approximately in the range of 0.5 to 5 cm. In one exemplary embodiment a maximum diameter of the flange of the distal portion 23 is approximately twice as large as a diameter of the flange of the proximal portion 21. The size of any portion of the retractor 20, or any other portion of the surgical device 10 for that matter, can be adjusted based at least on the intended use of the device 10.

Optionally, the retractor 20 can include one or more features to assist with the insertion of the retractor 20 into a surgical opening. In the illustrated embodiment an inflatable bladders 28 is included in the distal portion 23 of the retractor 20. A fluid can be selectively injected into the bladders 28 to help flip the distal portion 23 outward in a direction F during deployment of the retractor 20. Although injecting fluid into the bladders 28 can assist in expanding the distal portion 23 so that it can retract tissue and provide a seal between a surgical location and an outside environment as desired by a user, a user can selectively inject and remove fluid from the bladders 28 in order to achieve a number of desired configurations of the distal portion 23 of the retractor 20 with respect to the tissue in which it is disposed.

One or more seal elements can be disposed in the retractor 20. In the illustrated embodiment, three seal elements 30, 40, and 50 are disposed within the lumen 19 of the retractor 20. The seal elements 30, 40, and 50 can have bodies 32, 42, and 52 and can be generally configured to both receive instruments through a sealable opening 38, 48, and 58 formed in the bodies 32, 42, and 52, respectively, for use at a surgical site and to maintain a seal between a surgical site and an outside environment, thereby limiting or preventing fluid from passing therebetween.

The seal elements 30, 40, 50 can have a variety of shapes, sizes, and features, depending at least in part on the size of the incision and/or retractor in which they will be disposed, the surgical device components and instrument with which they will be used, and the type of surgical procedure with which they will be used. In the illustrated embodiment of FIG. 1 the seal elements 30, 40, and 50 are generally elongate and rectangular. A slit in each of the bodies 32, 42, 52 of the seal elements 30, 40, 50 forms the sealable openings 38, 48, 58. While in the illustrated embodiment each of the seal elements 30, 40, 50 is approximately the same size and shape, in alternative embodiments one or more of the seal elements can have a different size and/or shape than the other seal elements. While the size of the seal elements 30, 40, 50 can vary, and can depend at least in part on the size of the surgical opening and/or retractor in which they are disposed and the type of instrument(s) that will be disposed therein during a surgical procedure, in one exemplary embodiment they have a length approximately in the range of 1.5 to 3.5 centimeters, a height approximately in the range of 2 to 7 centimeters, and a thickness approximately in the range of 6 to 12 millimeters.

The seal elements 30, 40, 50 can also be made of a variety of materials, but generally can be configured to be flexible. Flexibility of the seal elements 30, 40, 50 can assist the seal elements 30, 40, 50 in allowing the instrument to make desired movements while disposed in the seal element and still maintain the desired seal. Flexibility of the seal elements 30, 40 50 can also allow the seal elements to be configured and oriented in a variety of different shapes and sizes. By way of non-limiting example, in one embodiment the seal elements can be configured to adapt an "s" shape, as shown by seal element 50 in FIG. 1. The size and shape of the seal elements 30, 40, 50 can be adjusted over the course of a surgical procedure, and can be adjusted depending on a variety of factors, including but not limited to the size of the incision and/or retractor in which they will be disposed, the surgical device components and instrument with which they will be used, the type of surgical procedure with which they will be used, the flexibility of the material of the seal elements, the hardness of the material of the seal elements, the orientation desired by the user, and the number, size, and type of adjustment mechanisms associated with the seal elements. In one embodiment the seal elements 30, 40, 50 can be made of a flexible polymer. Examples of polymeric materials that can be used to form the bodies 32, 42, 52 of the seal elements 30, 40, 50 include polyisoprene, polyurthethane, and silicone. Although flexible, the seal elements 30, 40, 50 can also have some rigidity to help protect any instruments disposed therein and to maintain a general location of the seal elements 30, 40, 50 within the surgical opening and/or the retractor 20.

The seal elements 30, 40, 50 can be generally configured to maintain a seal between the surgical site and an outside environment. One way in which a seal can be maintained is by way of the sealable openings 38, 48, 58. The sealable openings 38, 48, 58 can be configured to form a seal itself when no instrument is disposed therein, and to conform to and seal around an instrument disposed within the sealable opening. In the illustrated embodiment, each of the seal elements 30, 40, and 50 includes an instrument 105, 106, and 107 disposed therein. The instruments can have a variety of shapes and sizes. While in the illustrated embodiment the instrument 106 has a greater diameter than the instruments 105 and 107, in other embodiments the diameter of the instruments 105, 106, 107 can be similar or they can each be different. Diameters of the instruments 105, 106, 107 can generally be approximately in the range of 1 to 30 millimeters, and more particularly approximately in the range of 3 to 15 millimeters. In one exemplary embodiment one of the instruments 105, 106, 107, such as instrument 106, can be configured to provide insufflation to the surgical site. Further, in some embodiments, such as when the seal elements are elongate, the seal elements can have different portions that seal against itself while other portions seal around an instrument disposed therein. Such a configuration can effectively create multiple sealable access points within a single seal element. A seal element can include any number of sealable access points that are independently sealable against itself or around an instrument disposed therein. Such a configuration can also be useful for disposing multiple instruments in a single seal element while maintaining a sealing engagement between the seal element and each of the instruments.

While the sealable openings 38, 48, 58 can be configured to conform and seal around a surgical instrument, they can also be configured to allow for movement of an instrument disposed therein while still maintaining the seal. Movement of an instrument can occur in any direction with respect to the sealable openings 38, 48, 58, and in more than one direction at a time, while still maintaining a seal between a surgical site and an outside environment. For example, the sealable openings 38, 48, 58 can be configured to allow for an instrument to move in a plane that is parallel to a surgical opening. The sealable openings 38, 48, 58 can also be configured to allow for an instrument to move in a plane that is perpendicular to a surgical opening. Other examples of directional movement include, but are not limited to, an angular direction and a vertical direction. Even as movement of an instrument occurs in the sealable openings 38, 48, 58, the sealable openings 38, 48, 58 can continue to maintain the seal between a surgical site, such as a body cavity adjacent to the surgical opening in which the seal elements 30, 40, 50 are disposed, and an outside environment.

In addition to forming a seal within the seal elements 30, 40, 50, a seal can also be formed between adjacent seal elements, between the seal elements and the retractor 20, and between the seal elements and the tissue in which the surgical opening is formed in embodiments in which a surgical access device does not include a retractor. To assist in the formation of these various seals, the seal elements 30, 40, 50 can include any number of mating features. In the illustrated embodiment each of the seal elements 30, 40, and 50 includes pliable hexagonal components 44, 54 (pliable hexagonal components of the seal element 30 are not visible) that are config-ured to mate to the adjacent seal element that also includes the pliable hexagonal components. The ability of the pliable hexagonal components to mate adjacent seal elements and mate seal elements to the retractor 20 and/or tissue, as well as other mating elements that can also be used to couple adjacent components of the surgical access device to each other or directly to tissue, is described in greater detail in U.S. Publication No. 2010/0312060 entitled "Interlocking Seal Components" of Shelton et al., and filed on Jun. 5, 2009, which is hereby incorporated by reference in its entirety. Mating elements such as the pliable hexagonal components can allow the seal elements 30, 40, 50 to be removable, replaceable, and interchangeable.

One or more mechanisms for manipulating a configuration of the seal elements 30, 40, 50, sometimes referred to as adjustment mechanisms, can be associated with the seal elements 30, 40, 50 in a manner that allows the mechanism(s) to assist in adjusting, changing, and/or manipulating an orientation and/or configuration of the seal elements 30, 40, 50 during the course of a surgical procedure. The types of orientations that can be adjusted include, but are not limited to, the size (such as length, width, thickness, etc.), shape, location, relationship with respect to other components of the device 10, such as the retractor 20, and relationship with respect to other aspects or components of the surgical procedure itself, such as the surgical instruments, the surgical opening, the tissue, etc. Manipulating the seal elements 30, 40, 50 by way of the adjustment mechanism(s) can adjust particular properties of the seal elements 30, 40, 50, including an angle of a attack, a lead-in, and other ease-of-use features. The seal elements can tilt in response to the adjustment mechanism(s). In some embodiments the adjustment mechanism(s) can help lock a portion of a seal element, or the entire seal element, around an instrument to hold it in place. This can allow a different portion of the seal element to receive another instrument while maintaining a location of the instrument held in place. This can also allow a separate seal element to receive another instrument while maintaining a location of the instrument held in place. The ability to lock one or more instruments in place can free up a surgeon's hands to perform other actions at the surgical site without worrying about holding an instrument in place or without having to be concerned about a constricted work space created by having an additional person or device holding an instrument in place.

In the embodiment illustrated in FIG. 1, the adjustment mechanism includes three inflatable bladders 62, 72, 82. A first bladders 62 can be disposed between the seal elements 30 and 40, a second bladders 72 can be disposed between the seal elements 40 and 50, and a third bladders 82 can be disposed between the seal element 50 and a sidewall of the retractor 20. The bladders 62, 72, 82 can have any shape or size, which can be adjusted in response to a fluid, and can be made of a variety of materials. In the illustrated embodiment the bladders 62, 72, 82 are generally elliptical, have a height approximately equal to a height of the seal elements 30, 40 50, a width that is approximately less than half a length of the seal elements 30, 40, 50, a thickness that is equal to or slightly less than a thickness of the seal elements 30, 40, 50, and is made from materials that are similar to the materials used to form the seal elements 30, 40, 50. Similar to the other components of the surgical access device 10, however, a size, shape, and material of the bladders 62, 72, 82 can depend, at least in part, on the size of the incision and/or retractor in which they will be disposed, the surgical device components and instrument with which they will be used, the type of surgical procedure with which they will be used, and the desired configurations and/or orientations of the seal elements. In one exemplary embodiment the bladders 62, 72, 82 have a height approximately in the range of 2 to 7 centimeters, a width approximately in the range of 1 to 2 centimeters, a thickness approximately in the range of 2 to 5 millimeters in an uninflated configuration and 10 to 30 millimeters in an inflated configuration, and can be made of a flexible material, such as polypropylene, polyethylene, isoprene, sanoprene, polyurthethane, and/or silicone. The bladders 62, 72, 82 can also include features that assist in maintaining the seal between the surgical site and an outside environment, such as the mating features discussed with respect to the seal elements 30, 40, 50. Mating features of the bladders 62, 72, 82 can mate to the seal elements 30, 40, 50, the retractor 20, or directly to tissue where desired.

Further, the arrangement of the bladders 62, 72, 82 with respect to the seal elements 30, 40, 50 can vary depending on many of the same factors that can affect the size, shape, and materials of the bladders 62, 72, 82. Thus, while in the illustrated embodiment the first bladders 62 is disposed approximately at an intermediate position along the seal elements 30 and 40, the second bladders 72 is disposed approximately at one end of the seal elements 40 and 50, and the third bladders 82 is disposed approximately at a second end of the seal element 50, a variety of configurations can be used, including configurations in which more than one bladders is disposed between the same seal elements, multiple bladders are substantially aligned, or multiple bladders are associated with the same seal element(s) to manipulate only a small portion of the seal element(s). The bladders 62, 72, 82 can be used to adjust the orientation of particular chambers or sections of seal elements adjacent thereto. A person having skill in the art will recognize that the number of different configurations of the seal elements 30, 40, 50 that the bladders 62, 72, 82 can form is generally limitless. By way of non-limiting example, by placing the second bladders 72 at one end of the seal element 50 and the third bladders 82 at a second end of the seal element 82 in the illustrated embodiment, a "s" shape of the seal element 50 can be achieved.

Once one or more adjustment mechanisms are associated with a seal element, the seal element can be actively adjusted during the course of a surgical procedure in order to achieve one or more desired orientations, such as the "s" shape. In the illustrated embodiment the bladders 62, 72, 82 can be expanded and contracted by adding or removing fluid therefrom. As shown with respect to the third bladders 82, a tube 84 can be coupled to the bladders 82 to place the bladders 82 in fluid communication with a fluid reservoir (not shown). Adding fluid to the bladders 82 can cause the bladders 82 to expand, thereby deflecting the seal element 50 in a desired manner. Likewise, removing fluid from the bladders 82 can cause the bladders 82 to contract, thereby moving the seal element 50 away from the deflected position. While in the illustrated embodiment the tube 84 provides the fluid from a reservoir, in other embodiments the bladders 62, 72, 82 can include a plurality of chambers with fluid disposed therein. The chambers can be configured to move fluid between the chambers of the individual bladders 62, 72, 82 to created desired orientations for the respective bladders 62, 72, 82. Such an embodiment requires mechanism for adjusting the seal elements 30, 40, 50 that is disposed outside of the retractor 20.

One way in which the flow of fluid into the inflatable bladders 62, 72, 82 can be regulated is by way of a seal control mechanism. A seal control mechanism can be in fluid communication with the bladders 62, 72, 82 to actively control the fluid that flows into and out of the bladders 62, 72, 82. In alternative embodiments a seal control mechanism can be in direct fluid communication with one or more seal elements 30, 40, 50 of the surgical access device 10 to actively and directly control an orientation or configuration of the seal elements 30, 40, 50. A person having skill in the art will recognize that in some instances the use of an adjustment mechanism and a seal control mechanism can be interchangeable, or further, the mechanisms can be integrally formed. More particularly, by way of non-limiting example, in embodiments in which fluid is applied directly to a seal element to adjust the orientation of the seal element, the mechanism applying the fluid to the seal element can serve as both an adjustment mechanism because the fluid adjusts the orientation of the seal element, and a seal control mechanism because the direct flow of fluid to the seal element can be regulated by the same component.

Figure 2:
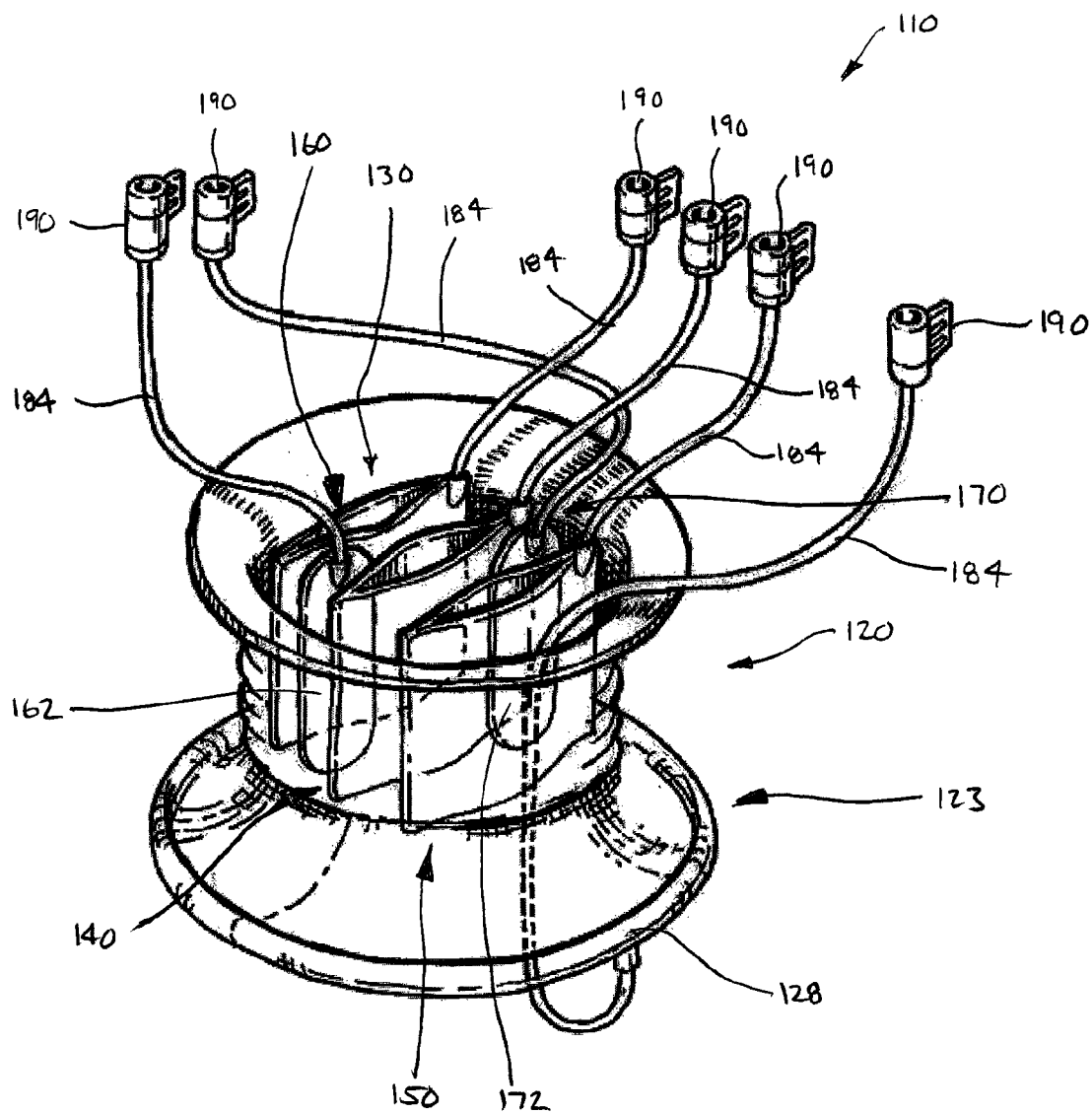
FIG. 2 is a perspective view of another exemplary embodiment of a surgical access device.
Figure 3:
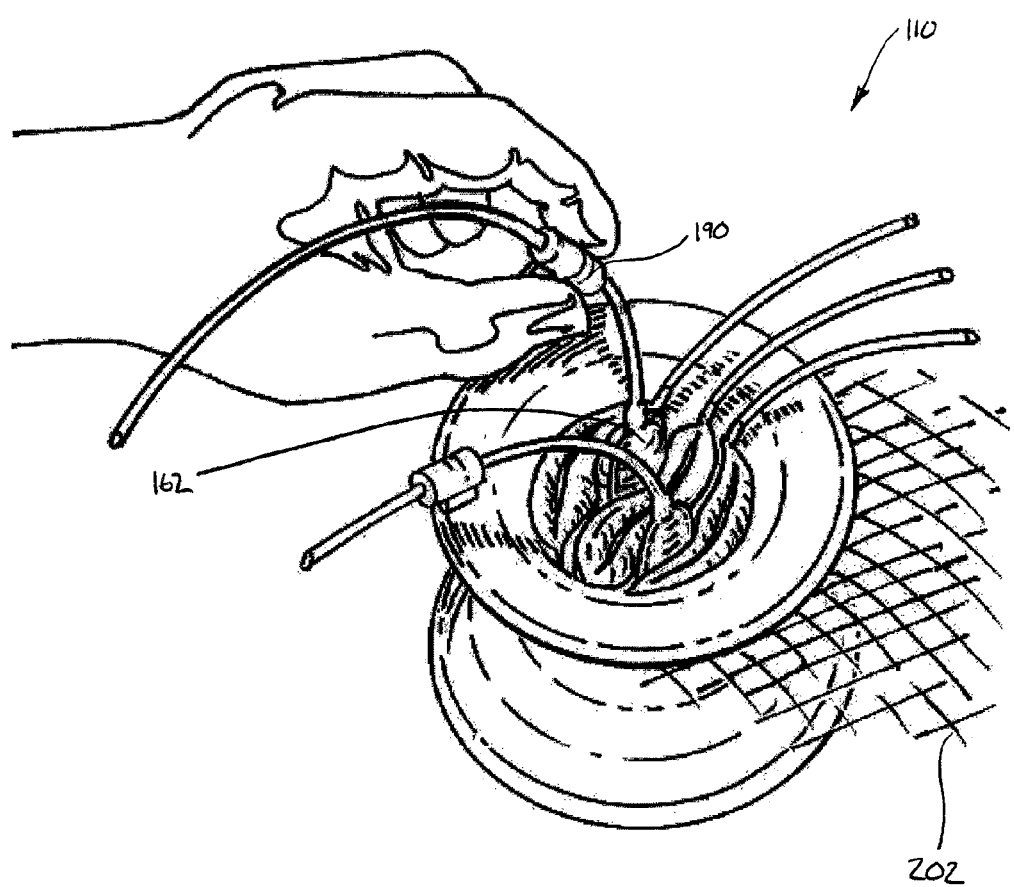
FIG. 3 is a top perspective view of the surgical access device of FIG. 2 disposed in a surgical opening in tissue.

In one embodiment of a surgical access device 110, shown in FIGS. 2 and 3, the device 110 includes a retractor 120, three elongate seal elements 130, 140, 150 disposed within at least a portion of the retractor 120, two adjustment mechanisms 160 and 170, in this instance two inflatable bladders 162, 172, disposed between the first and second seal elements 130, 140 and the second and third seal elements 140, 150, respectively, and seal control mechanisms coupled to each of the seal elements 130, 140, 150, the inflatable bladders 162, 172, and a distal portion 123 of the retractor 120. As shown, the seal control mechanisms are a series of valves 190 coupled to each of the aforementioned components of the surgical access device 110 by way of tubes 184. Fluid can be added or removed from each of the components that are coupled to the valves 190 as desired. Thus, an orientation and/or configuration of the seal elements 130, 140, 150 can be controlled by way of fluid flow to any combination of components of the surgical access device 110, including the flow of fluid directly to the seal elements 130, 140, 150 themselves and the flow of fluid to the bladders 162, 172 disposed adjacent to the seal elements 130, 140, 150. Alternatively, the valves 190 can be linked to an insufflation valve and an insufflation device can be used to inflate and/or deflate the various components of the surgical access device 110. FIG. 2 also illustrates that a valve 190 and tube 184 can optionally be coupled to the distal portion B123 of the retractor 120. As discussed with respect to the surgical access device 10 of FIG. 1, a fluid can be added to or removed from a bladders 128 located in the distal portion 123 of the retractor 120 to assist in positioning the retractor 120 in a desired location.

The bladders, and any component associated with either an adjustment mechanism or a seal control mechanism, can be adjusted individually, or alternatively, they can be adjusted simultaneously. Thus, a single bladders can be expanded or contracted as desired or more than one bladders, including all of the bladders used as an adjustment mechanism, can be expanded and/or contracted at the same time. Further, adjustments can be made based on a manual input, or alternatively, adjustments can be made based on one or more automatic inputs. For example, a surgeon can elect to expand or contract one or more bladders in order to achieve a desired orientation of the seal element(s). In particular, the surgeon can control the flow of fluid into and out of the bladders directly and instantaneously.

FIG. 3 illustrates an embodiment in which the surgical access device 110 is disposed in a surgical opening 204 in tissue 202 and a flow of fluid is manually adjusted by way of the valve 190 coupled to the inflatable bladders 162. Alternatively, the bladders can be configured to respond to one or more conditions and/or components and fluid can be added or removed to the bladders in order to create a desired configuration and/or orientation of the seal element(s). For example, the bladders can be configured to create a particular orientation of the seal element(s) based on a particular programmed time. Alternatively, the bladders can be configured to create a particular orientation of the seal element(s) in response to a particular surgical condition that is sensed by the surgical access device. Any number of devices capable of sensing desired conditions can be easily incorporated to the various components of the surgical access device. In another example the bladders can be programmed to form a number of different desired orientations of the seal element(s). More particularly, each orientation can be pre-programmed, and then a user can select a particular orientation, and the bladders can coordinate to expand and/or contract in order to achieve the programmed orientation. By way of further non-limiting example, the bladders can be configured to create a particular orientation based on the particular instrument that is disposed in the seal element. More particularly, the instrument can include an identifier that allows the bladders to recognize when a particular instrument is disposed in a seal element and then fluid can be added or removed from the bladders in order to form an orientation that is desired for that particular instrument. A person skilled in the art would recognize that the types of triggers that can be implemented into the surgical access device are virtually limitless and can be configured to be associated with any component of the device, such as the retractor, the seal elements, and/or the bladders, as well as any component used in conjunction with the device, such as surgical instruments.

A person skilled in the art will recognize that while the illustrated embodiments include two and three bladders, any number of bladders, including zero, one, or four or more, can be used. Likewise, the bladders can be associated with any portion or any seal element in order to form any number of orientations and configurations. The ability to actively adjust the orientation and/or configuration of a particular seal element or a group of seal elements at a surgical location allows for a virtually limitless number of configurations to be achieved. Further, although the illustrated embodiment generally discusses the use of inflatable bladders to create desired configurations, any number of different mechanisms can be used to actively change an orientation of a seal element and a configuration of a group of seal elements, some of which are discussed below.

Figure 4A:
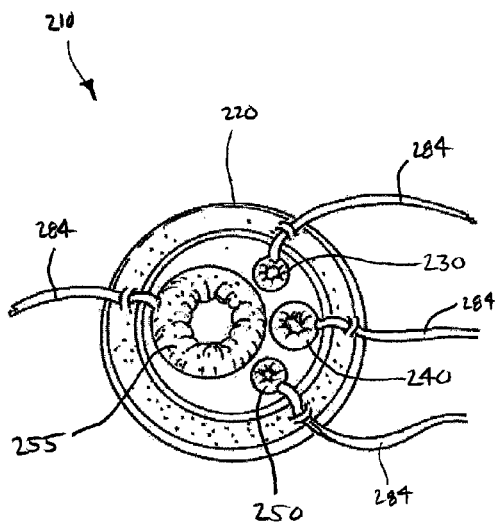
FIG. 4A is a top perspective view of still another exemplary embodiment of a surgical access device.
Figure 4B:
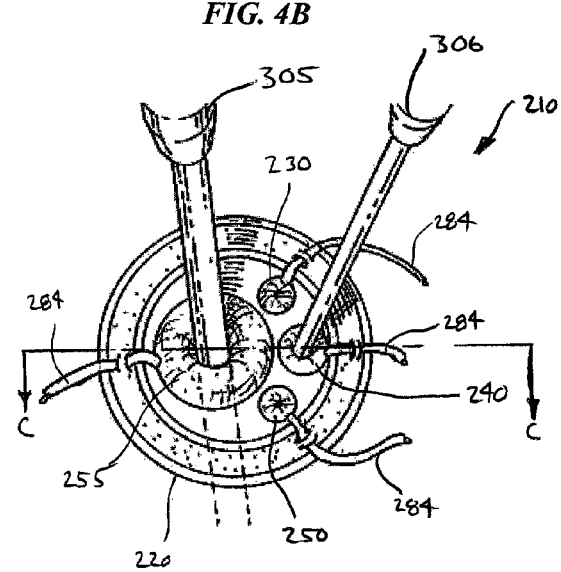
FIG. 4B is a top perspective view of the surgical access device of FIG. 4A having surgical instruments disposed in seal elements of the surgical access device.
Figure 4C:
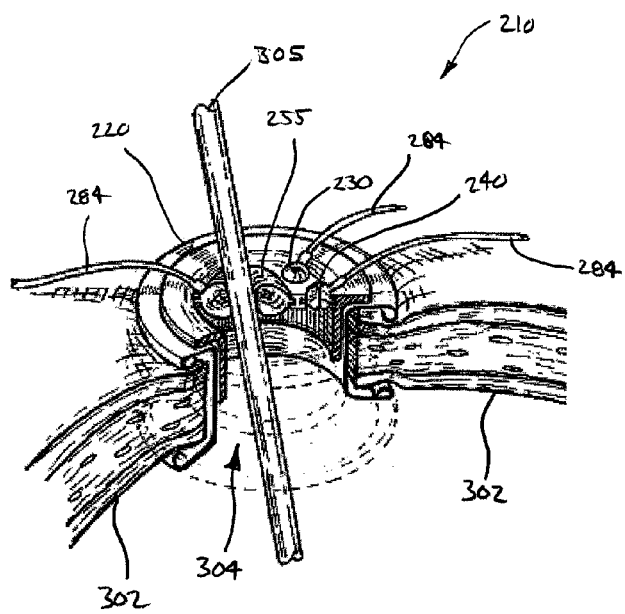
FIG. 4C is a perspective cross-sectional view of the surgical access device of FIG. 4B taken along line C-C with the device disposed in a surgical opening in tissue.

In an alternative embodiment of a surgical access device 210, illustrated in FIGS. 4A-4C, the adjustment mechanism and the seal control mechanism can be one in the same, and thus manipulating a configuration and/or orientation of a seal element can be achieved by directly controlling various properties of the seal elements. As shown, the surgical access device 210 includes a retractor 220 having a plurality of seal elements 230, 240, 250, 255 disposed in at least a portion of the retractor 220 and an adjustment mechanism (not shown) coupled directly to each of the seal elements 230, 240, 250, 255 by way of tubes 284. Fluid can be regulated by the adjustment mechanisms to adjust a configuration and/or orientation of the respective seal elements 230, 240, 250, 255. For example, a size of a port of each of the seal elements 230, 240, 250, 255 can be changed by adding or removing fluid from the seal elements 230, 240, 250, 255. The retractor 220 can be configured to be positioned within a surgical opening 304 in tissue 302 for use during any number of surgical procedures. As shown, there are four seal elements 230, 240, 250, 255, and each has a rounded configuration. Elongate seal elements, like those discussed with respect to the surgical access devices 10, 110 of FIG. 1 and FIGS. 2-3, respectively, can also be used. Further, other types of seal elements can also be used in any of the configurations discussed herein, including but not limited to gel, multi-layer, duckbill, gimbal, zero-closure, diaphragm, and septum seal elements, each of which can serve particular purposes.

The surgical access device of FIGS. 4A-4C has many of the same capabilities of the surgical access devices 10, 110 of FIG. 1 and FIGS. 2-3. Accordingly, one or more instruments 305, 306 can be disposed in the seal elements 230, 240, 250, 255, as shown seal elements 240 and 255, and a configuration of the seal elements 230, 240, 250, 255 can be controlled based on a variety of factors, including but not limited to the size of the incision and/or retractor in which they will be disposed, the surgical device components and instrument with which they will be used, the type of surgical procedure with which they will be used, the flexibility of the material of the seal elements, the hardness of the material of the seal elements, the orientation desired by the user, and the number, size, and type of adjustment mechanisms associated with the seal elements. Further, similar to the surgical access devices 10, 110 of FIG. 1 and FIGS. 2-3, manipulation of the seal elements 230, 240, 250, 255 can occur individually, simultaneously, manually, and/or automatically.

Figure 5:
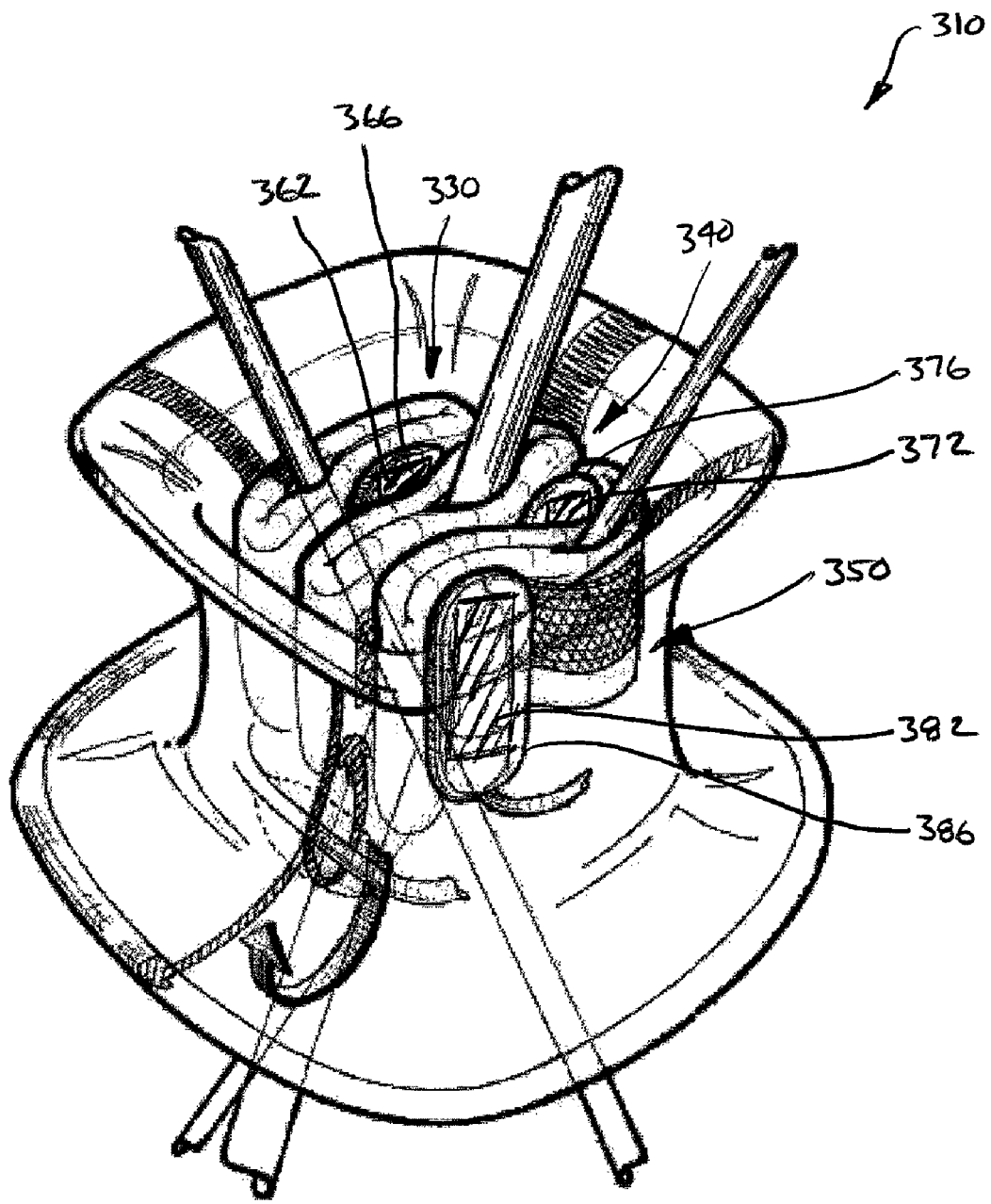
FIG. 5 is a partially transparent perspective view of yet another exemplary embodiment of a surgical access device.

Not only can a variety of different seal elements be used in conjunction with the teachings herein, but so can a number of different adjustment mechanisms and/or seal control mechanisms. A variety of different mechanical, electrical, electro-mechanical, chemical, and biological configurations can be used to actively adjust a seal element configuration and/or orientation. By way of non-limiting example, in one embodiment, shown in FIG. 5, an adjustment mechanism can include one or more stacks of electro-active polymers (EAPs) 362, 372, and 382 that can be conductive doped polymers that change shape when electrical voltage is applied. The conductive doped polymers can be paired to some form of ionic fluid or gel and electrodes. A voltage potential can be applied to the polymers to induce a flow of ions from the fluid/gel into or out of the conductive polymer, which in turn can induce a shape change of the polymer. As the polymer changes shape, it can manipulate a configuration and/or orientation of seal elements 330, 340, 350 that the EAPS 362, 372, 382 are disposed adjacent to, similar to the bladders 62, 73, 82 and 162, 172 of the devices of FIGS. 1 and 2-3, respectively. In one embodiment, a size of a stack of EAPs 362, 372, 382 can increase or decrease in size by approximately a range of 30 to 50 percent. A shell 366, 376, 386 can be disposed around one or more stacks of EAPs 362, 372, 382 to help constrain the EAPs 362, 372, 382 from expanding into undesired locations. For example, the shells 366, 376, 386 can help prevent the EAPs 362, 372, 382 from expanding vertically into a surgical cavity. In one exemplary embodiment the shells 366, 376, 386 can be made of a material like a polycarbonate. Alternatively, the seal elements themselves can include one or more stacks of EAPs, thus changing the configuration and/or orientation of the seal elements directly. In such an embodiment an outer diameter of the seal elements can be made of a rigid material, such as a polycarbonate, to act as a shell to prevent or limit expansion or vertical growth, and an inner diameter can include EAPs. Thus, when a voltage potential is applied to the EAPs near the inner diameter, the EAPS can only expand or move in a single designated direction. The more voltage potential that is applied can generally lead to a smaller inner diameter of the seal element.

The voltage potential can approximately range from 1 V to 4 kV, depending at least on the polymer and ionic fluid used. Some EAPs can be configured to contract when voltage is applied while other EAPs can be configured to expand when voltage is applied. Two types of EAPs that can be used in conjunction with the teachings herein are a fiber bundle and a laminate version. Further detail about each of these types, as well as other features of EAPs that can be used in conjunction with the teachings herein, can be found in U.S. Patent Application Publication No. 2006/0025813 of Shelton et al., filed on Jun. 1, 2005, and entitled "Surgical Stapling Instrument Having an Electroactive Polymer Actuated Medical Substance Dispenser," which is hereby incorporated by reference in its entirety. Further, a person skilled in the art will recognize that in alternative embodiments the EAPs can be coupled to other mechanical components, such as springs or flexible plates, to assist in adjusting the configuration and/or orientation of the seal elements.

Figure 6:
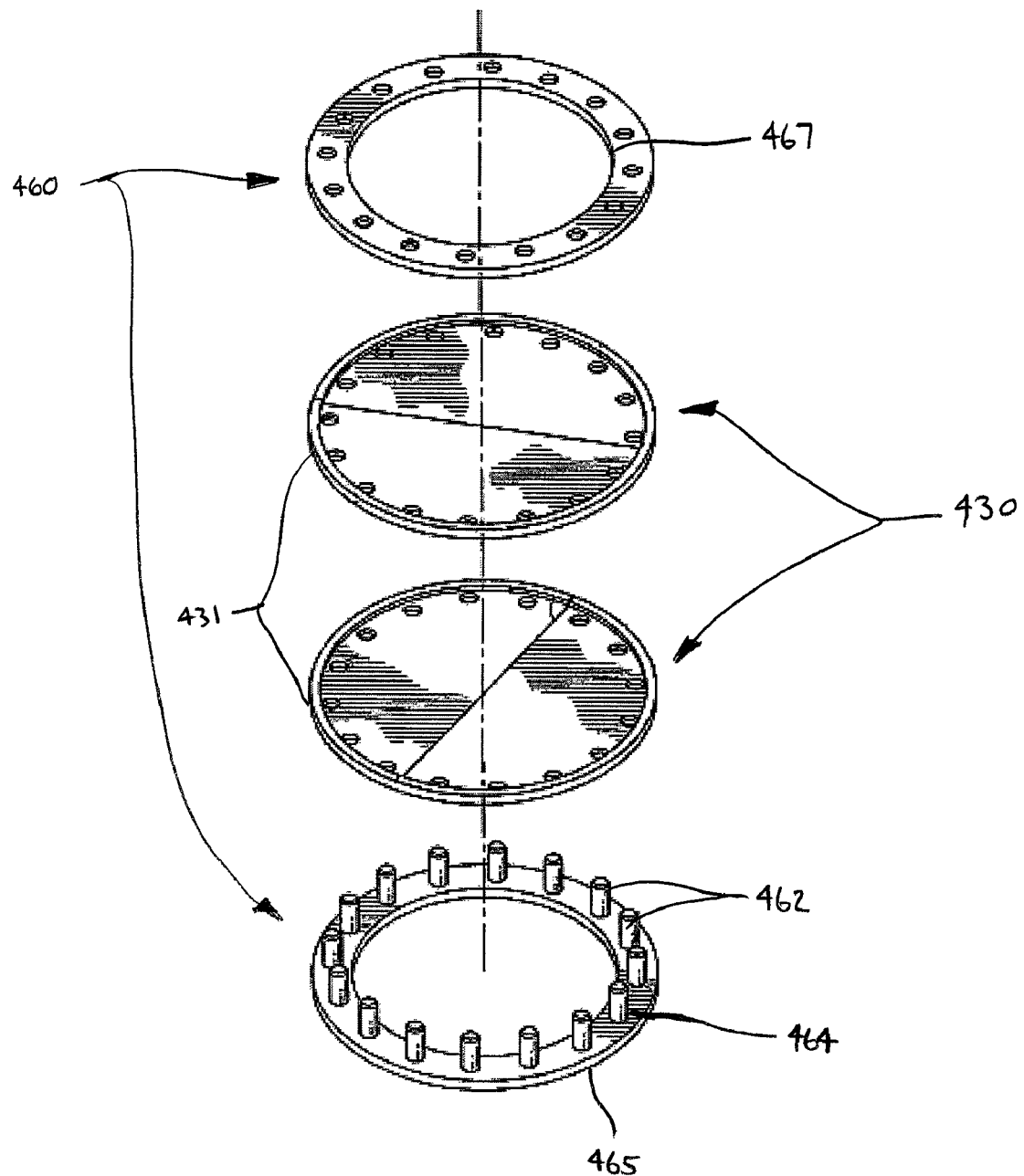
FIG. 6 is an exploded view of a seal element of a surgical access device having an adjustment mechanism that is a dilatable ring.

A seal control mechanism that includes EAPs is just one example of electro-mechanical components that can be used to actively manipulate seal elements. Likewise, a number of fully mechanical components can also be used to actively manipulate seal elements. For example, a variety of different linkage systems can be coupled to the seal elements to allow for a variety of different orientations and/or configurations of the seal elements. One such system can be a four-bar linkage that is expandable and retractable in a tent-like fashion. By way of further non-limiting example, in another embodiment a seal control mechanism can incorporate an umbrella-like design. One example of such a design is shown in FIG. 6 and includes a seal control mechanism 460 coupled directly to a seal element 430 to constrain particular portions of the seal element 430. While the seal element 430 can have a variety of shapes, in the illustrated embodiment the seal element 430 is generally circular. The seal control mechanism 460 can be configured to constrain an outer diameter 431 of the seal element 430, for instance by way of a static lock-pin arrangement 462. The lock-pin arrangement 462 can be formed on a dilatable iris-like ring 464 such that twisting an outer diameter 465 of the ring 464 about a main axis of the ring 464 can expand or contract an inner diameter 467 of the ring 464 because the seal element 430 is disposed between the inner and outer diameters 467, 465 of the dilatable ring 464. This, in turn, can allow the seal element 430 itself to expand or contact along with the inner diameter 467 of the ring 464. Further details and embodiments of such a set-up are more thoroughly discussed in U.S. Pat. No. 7,481,795 of Thompson et al., which is hereby incorporated by reference in its entirety. A person having ordinary skill in the art will recognize that in alternative embodiments umbrella-like designs can be utilized as separate seal control mechanisms disposed adjacent to the seal elements such that expansion and contraction of the seal control mechanism can in turn manipulate a configuration and/or orientation of the adjacent seal elements. Further, such designs can also be coupled to other mechanical components, such as springs, linkages, and plates, to transfer the energy created by the dilatable ring to the seal element to adjust the orientation of the seal element.

In use, the surgical access device can enable a surgeon to easily manipulate a size, shape, and/or configuration of one or more seal elements of the surgical access device for any number of desired procedures. For convenience, when discussing various methods of using surgical access devices, rather than reciting each of the various embodiments of surgical access devices and their related components, reference will be made to the surgical access devices 110, and their respective components, of FIGS. 2 and 3, unless otherwise stated. A person skilled in the art will recognize that the methods discussed herein can generally be adapted for other embodiments discussed herein.

An incision or opening 204 can be formed in a tissue 202 of a body. For example, an incision can be formed in an abdominal wall. A retractor 120 having one or more seal elements 130, 140, 150 disposed therein and one or more adjustment mechanisms 160, 170 for manipulating an orientation of one or more of the seal elements 130, 140, 150 can be positioned in the opening 204 and engage tissue 202 surrounding the opening 204 to retract the tissue 202. When the surgical opening is near an abdomen, for example, the retractor can retract the fascia layer. The retractor 120 can form a seal between the tissue 202 of the opening 204 and the retractor 120 itself. While the retractor 120 can be disposed in an incision in a number of ways, in one embodiment the retractor 120 can be folded or collapsed and inserted into and through the incision 204. A distal portion 123 of the retractor 120 can engage an inner surface of the tissue 202 and the remaining portion of the retractor 120 can be pulled back through the tissue 202 to securely engage the retractor 120 at least partially within the incision 204. Further, in embodiments in which one or more inflatable bladders 128 are incorporated with the distal end 123 of the retractor 120, the bladders 128 can be selectively inflated and deflated in order to position the distal end 123 of the retractor 120 in a desired location. Inflating the bladders 128 can assist in securing the distal end 123 against the tissue 202 to perform the desired tissue retraction, as well as form the desired seal between the retractor 120 and the tissue 202.

Optionally, the surgical access device 110 can include one or more seal control mechanisms. The seal control mechanisms can be used to selectively adjust the configuration and/or orientation of the adjustment mechanisms 160, 170. As illustrated, in FIGS. 2 and 3, the adjustment mechanisms 160, 170 are inflatable bladders 162, 172 and the seal control mechanisms are valves 190 that regulate the flow of fluid into and out of the adjustment bladders 162, 172. A surgeon can use the valves 190, or other mechanisms for controlling the adjustment mechanisms 160, 170 used to manipulate the orientations of the seal elements 130, 140, 150, in order to achieve a desired configuration.

An instrument can be inserted into one or more openings 138, 148, 158 of the seal element 130, 140, 150 to allow the instrument to access the surgical site. Alternatively, multiple instruments can be disposed in the same seal element and/or more than one seal element can each receive one or more instruments therein. Thus, any number of surgical procedures can be performed. Generally, the openings 138, 148, 158 of the seal element 130, 140, 150 can be configured to seal directly around the instrument to limit or prevent fluid from passing between the surgical site and the outside environment. The instrument can be manipulated and used as desired. In one embodiment, one of the instruments can be used to insufflate the surgical site.

At any time during the surgical procedure, the orientations and configurations of the seal elements 130, 140, 150 of the surgical access device 110 can be adjusted. Adjustments to the seal elements 130, 140, 150 can be achieved by way of any number of adjustment mechanisms, including the adjustment mechanisms discussed herein. Thus, a configuration of the seal element 130, 140, 150 can be changed by expanding or contracting inflatable bladders 162, 172 by adding or removing fluid from the bladders 162, 172.

Any number of properties of the seal elements 130, 140, 150 can be adjusted, including but not limited to their shape, size, and location relative to other seal elements 130, 140, 150 and/or the retractor 120. Any number of adjustment mechanisms 160, 170 can be manipulated at a time, and thus any number of seal elements 130, 140, 150 can be manipulated at a time. As discussed above, adjustments can also occur based on manual inputs or pre-programmed inputs, depending, at least in part, on the preference of the surgeon. The resulting configurations and orientations are virtually limitless, and each seal element 130, 140, 150 can have a different desired configuration that can be achieved at the same instance in time. In some embodiments the seal elements 130, 140, 150 can be manipulated in such a manner that an instrument can be held in place by a configuration formed in one portion of a seal element while another instrument can be used at the surgical site. The other instrument can be disposed in a separate seal element, or it can be inserted in the same seal element in which the instrument being held in place is disposed.

While in the illustrated embodiment manipulation of the seal elements 130, 140, 150 is achieved by way of the inflatable bladders 162, 172, in other embodiments a configuration and/or orientation of the seal elements 130, 140, 150 can be adjusted by other types of adjustment mechanisms, including but not limited to some of the other embodiments disclosed herein. By way of non-limiting example, and now referring to FIG. 5, a configuration of at least one seal element 330, 340, 350 can be achieved by applying a voltage to EAPS 362, 372, 382 coupled and/or adjacent to the seal elements 330, 340, 350. Alternatively, and now referring to FIG. 6, an orientation of at least one seal element 430 can be achieved by rotating a ring 464 coupled and/or adjacent to the seal element 430. Rotating of the ring 464 can cause the seal element 430 to expand or contract, as discussed in greater detail above. Still further, in some embodiments seal elements of a retractor themselves can include the seal adjustment mechanism. For example, and now again referring to FIGS. 2 and 3, the seal elements 130, 140, 150 can be configured to receive fluid, and thus rather than, or in addition to, expanding or contracting the bladders 162, 172 to change an orientation of one or more of the seal elements 130, 140, 150, the seal elements 130, 140, 150 themselves can be expanded or contracted directly by fluid. A person having ordinary skill in the art will recognize that these methods are not mutually exclusive, and thus seal elements and adjustment mechanisms can each be adjusted to affect the overall configuration and/or orientation of the seal elements.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
    a retractor configured to be positioned within a surgical incision to provide access to a body cavity, the retractor having a sidewall defining a central lumen;
    a plurality of seal elements disposed within the lumen of the retractor in a configuration effective to seal the lumen, each seal element having a sealable opening configured to receive a surgical instrument in a sealing engagement;
    at least one adjustment mechanism in communication with at least one seal element of the plurality of seal elements and configured to manipulate an orientation of one or more of the plurality of seal elements.

2. The surgical access device of claim 1, wherein the adjustment mechanism is one of an expandable bladder and an electroactive polymer, and wherein the adjustment mechanism is positioned adjacent to the at least one seal element of the plurality of seal elements.

3. The surgical access device of claim 2, wherein the expandable bladder and the electroactive polymer are configured such that expansion and/or contraction thereof controls the configuration of the plurality of seal elements.

4. The surgical access device of claim 1, wherein the adjustment mechanism comprises a valve configured to regulate an amount of fluid in at least one seal element of the plurality of seal elements.

5. The surgical access device of claim 1, wherein the openings of the plurality of seal elements are one of an elongate opening and a substantially circular opening.

6. The surgical access device of claim 1, further comprising a seal control mechanism in communication with the at least one seal element of the plurality of seal elements and the at least one adjustment mechanism.

7. The surgical access device of claim 1, wherein the plurality of seal elements is removably and replaceably mounted in the retractor.

8. A surgical access device, comprising:
    a retractor having a sidewall defining a central lumen;
    a plurality of seal elements disposed within the central lumen in a configuration effective to seal the lumen, each seal element having a sealable opening configured to receive a surgical instrument in a sealing engagement;
    at least one shape-changing adjustment mechanism positioned adjacent to at least one seal element of the plurality of seal elements and configured to manipulate an orientation of one or more of the plurality of seal elements when the at least one shape-changing adjustment mechanism changes shape.

9. The surgical access device of claim 8, wherein the at least one shape-changing adjustment mechanism comprises an expandable bladder configured to change shape based on fluid disposed therein.

10. The surgical access device of claim 8, wherein the at least one shape-changing adjustment mechanism comprises an electroactive polymer configured to change shape based on an electrical voltage applied thereto.

11. The surgical access device of claim 8, wherein the sealable opening of the at least one seal element is an elongate opening.

12. The surgical access device of claim 8, wherein the plurality of seal elements are removably and replaceably mounted in the retractor.

13. A surgical access device, comprising:
   a retractor having a sidewall defining a central lumen; and
   a plurality of seal elements disposed within the central lumen in a configuration effective to seal the lumen, each seal element having a sealable opening configured to receive a surgical instrument in a sealing engagement, and at least one seal element of the plurality of seal elements being configured to receive a fluid therein to manipulate an orientation of one or more of the plurality of seal elements.

14. The surgical access device of claim 13, further comprising a valve coupled to the at least one seal element configured to receive a fluid therein, the valve being configured to regulate an amount of fluid in the at least one seal element.

15. The surgical access device of claim 13, wherein the sealable opening of the at least one seal element is substantially circular.

16. The surgical access device of claim 13, wherein the plurality of seal elements are removably and replaceably mounted in the retractor.

* * * * *